United States Patent
Stewart et al.

(10) Patent No.: US 12,138,421 B2
(45) Date of Patent: Nov. 12, 2024

(54) APPARATUSES AND METHODS FOR DETECTING USER FILL VOLUME IN MEDICATION DELIVERY DEVICE

(71) Applicant: Becton, Dickinson and Company, Franklin Lakes, NJ (US)

(72) Inventors: Scott Stewart, Pittsburgh, PA (US); Abigail Kruegle, Somerville, MA (US); Muzaffer Ozsecen, Groton, MA (US); J. Richard Gyory, Sudbury, MA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 188 days.

(21) Appl. No.: 17/591,398

(22) Filed: Feb. 2, 2022

(65) Prior Publication Data

US 2023/0241310 A1 Aug. 3, 2023

(51) Int. Cl.
*A61M 5/145* (2006.01)
*A61M 5/142* (2006.01)
*A61M 5/168* (2006.01)

(52) U.S. Cl.
CPC ...... *A61M 5/1452* (2013.01); *A61M 5/14244* (2013.01); *A61M 5/16804* (2013.01); *A61M 2205/3331* (2013.01); *A61M 2205/3553* (2013.01)

(58) Field of Classification Search
CPC ............ A61M 5/1452; A61M 5/14244; A61M 5/16804; A61M 2205/3331; A61M 2205/3553; A61M 5/16854; A61M 2205/073; B65B 3/003
See application file for complete search history.

(56) References Cited

U.S. PATENT DOCUMENTS

| | | | |
|---|---|---|---|
| 9,750,875 B2 | 9/2017 | Smith et al. | |
| 10,772,796 B2 | 9/2020 | Kavazov | |
| 11,173,242 B2 | 11/2021 | Lanigan et al. | |
| 2001/0018937 A1* | 9/2001 | Nemoto | A61M 5/1456 604/416 |
| 2013/0296786 A1* | 11/2013 | McConnell | A61M 5/16881 604/151 |
| 2016/0259913 A1* | 9/2016 | Yu | A61M 5/31511 |
| 2020/0022416 A1* | 1/2020 | Alarcon | A24F 40/57 |
| 2020/0238018 A1* | 7/2020 | Lee | A61M 5/31568 |

FOREIGN PATENT DOCUMENTS

| WO | WO-2002022190 A1 | 3/2002 |
|---|---|---|
| WO | WO-2021092284 A1 | 5/2021 |

* cited by examiner

*Primary Examiner* — Scott J Medway
*Assistant Examiner* — Anh Bui
(74) *Attorney, Agent, or Firm* — Dickinson Wright PLLC

(57) ABSTRACT

A medication delivery device includes an infusion pump system having a reservoir, a fluid path connected between the reservoir and an insertion mechanism, a plunger arranged inside the reservoir, and a pump drive mechanism coupled with the reservoir. The medication delivery device further includes a processing device configured to determine a user fill volume of a fluid medication by analyzing a location of the plunger inside the reservoir when a fill of the fluid medication is completed. The processing device is configured to determine the user fill volume of the fluid medication by sensing a pressure inside the reservoir.

13 Claims, 9 Drawing Sheets

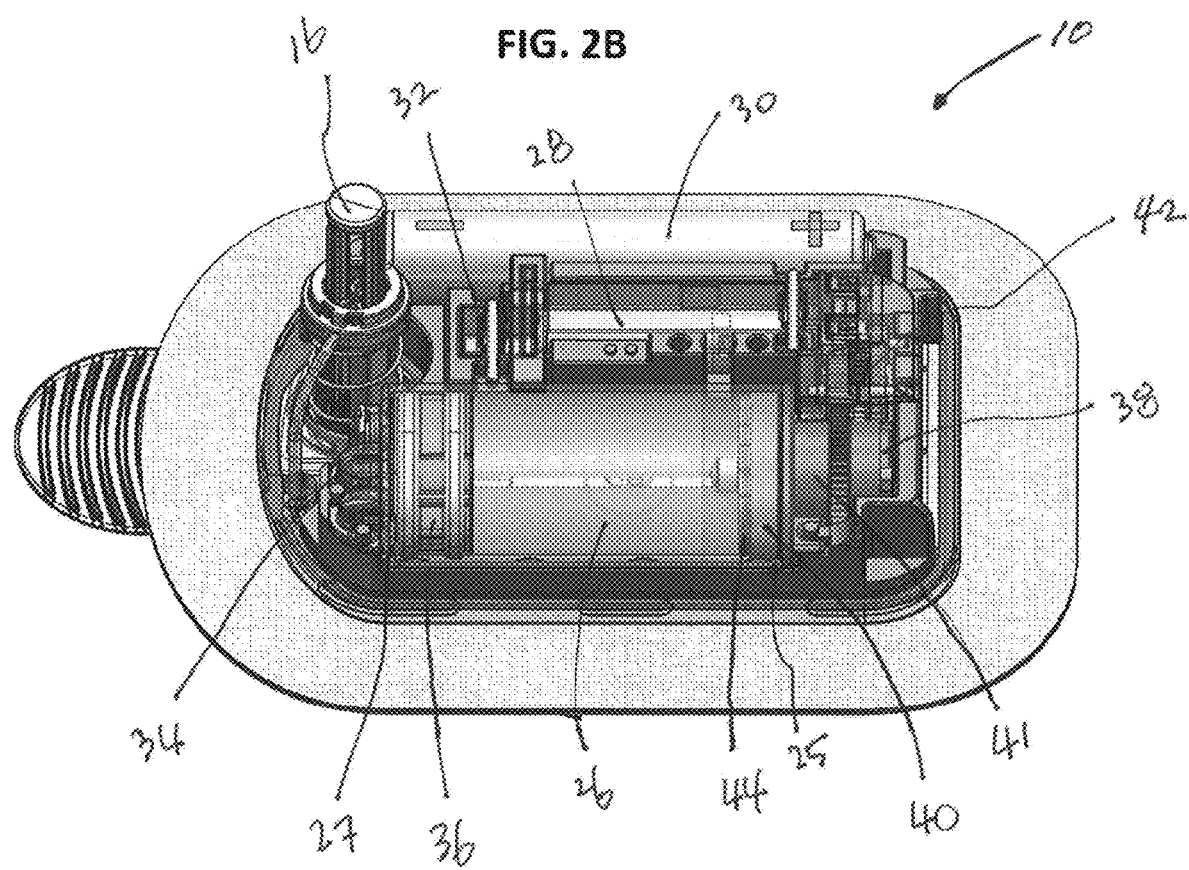

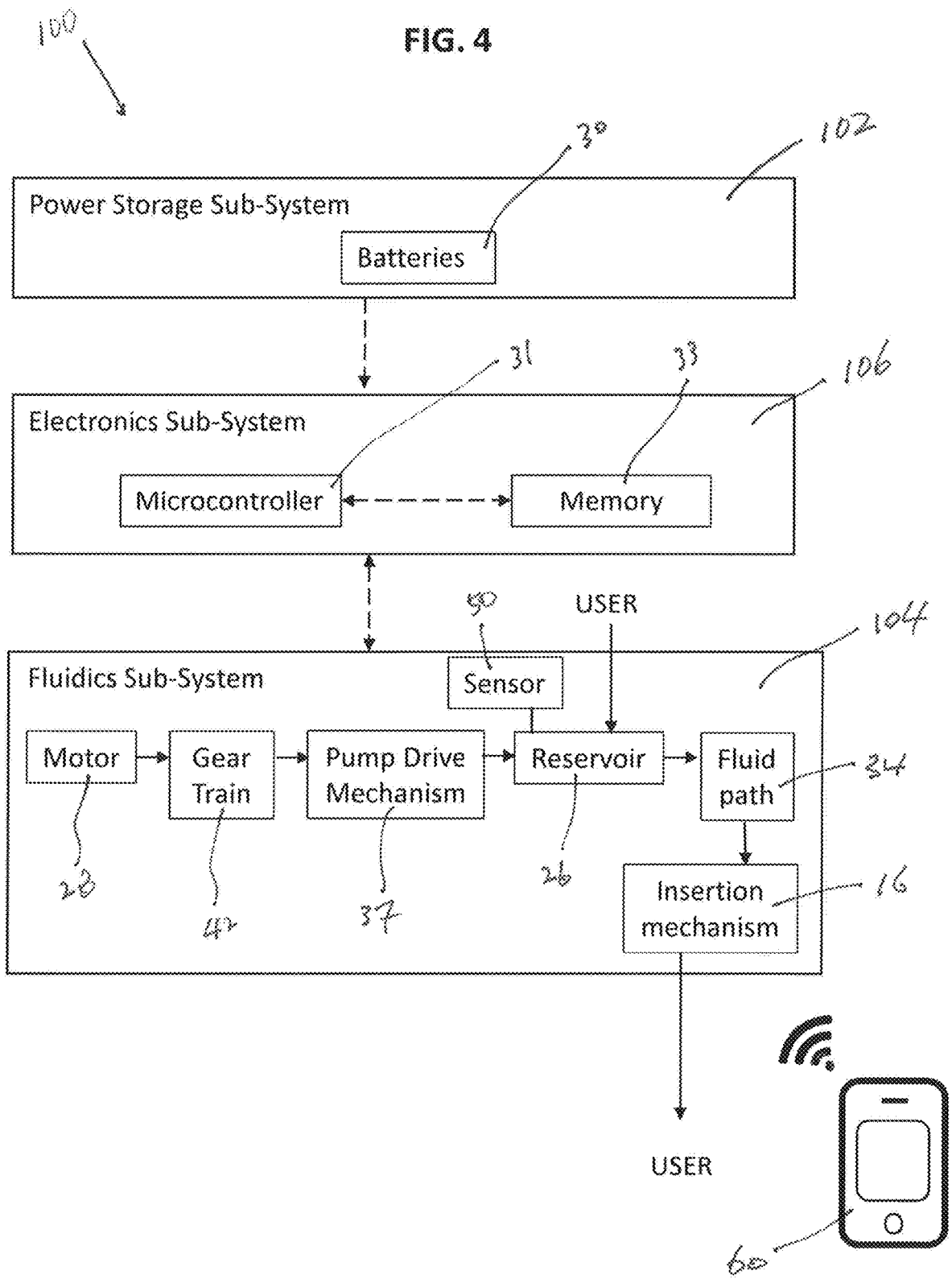

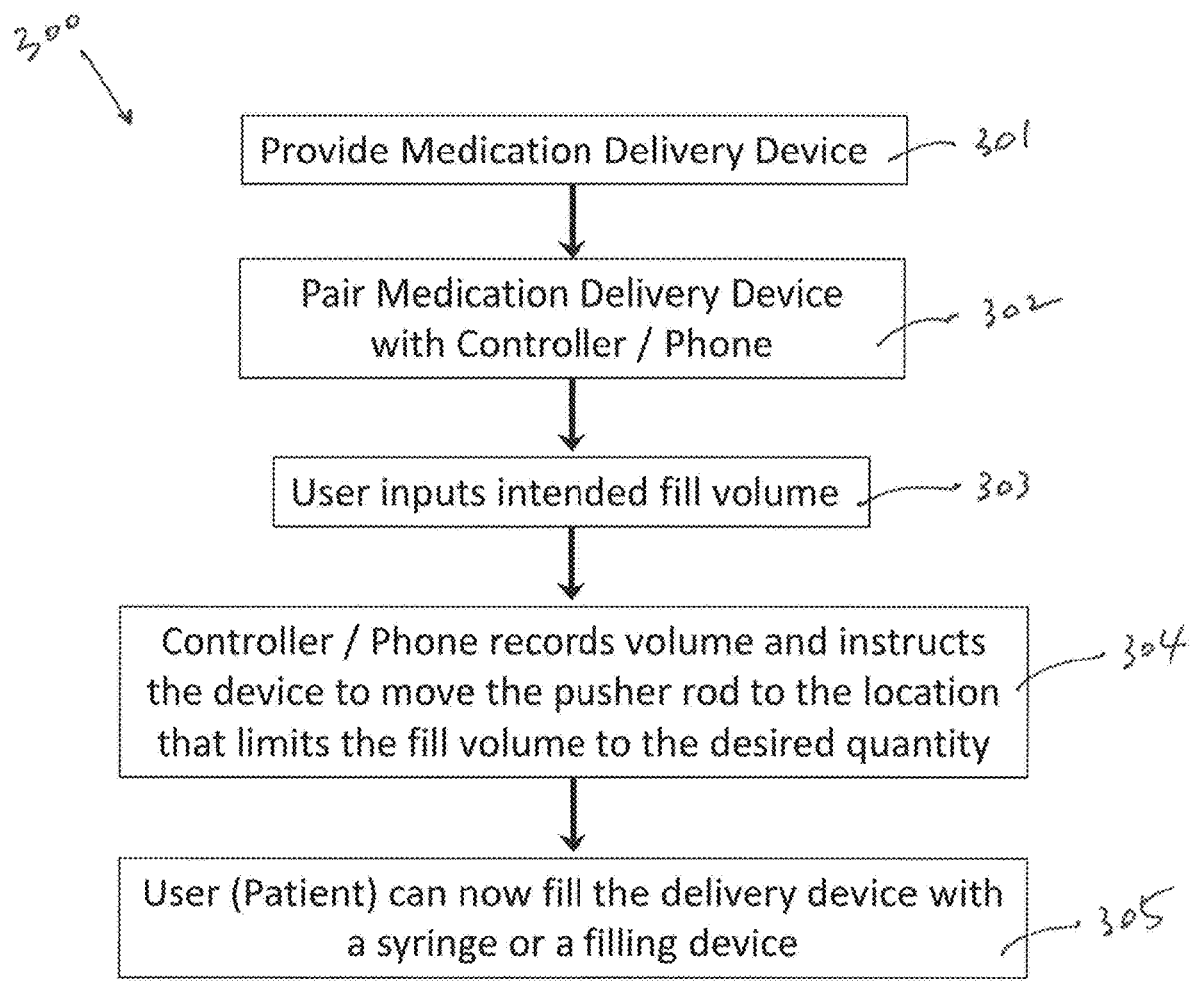

APPARATUSES AND METHODS FOR DETECTING USER FILL VOLUME IN MEDICATION DELIVERY DEVICE

FIELD

The present disclosure relates to medical devices, and more particularly to medication delivery devices with an infusion pump system for detecting a user fill volume of a fluid medication.

BACKGROUND

Infusion pumps generally have a reservoir with a known volume of fluid medication and known dispense stroke volume to count down doses to estimate how much fluid fills in the reservoir by a user. Without knowing precisely the volume of fluid in the reservoir, a user cannot know how much fluid medication is filled in the reservoir each time. So the users always need to measure the amounts of the medication each time when filling the reservoir, which is burdensome.

Typical methods for determining user fill volume inside the reservoir are expensive and potentially burdensome. For example, some infusion pumps have a separate filling device that measures a precise fill and wirelessly communicates the fill amounts to the main pump or controller. Other infusion pumps don't measure input fill, but have a method for counting down from a specific point (for example, some devices count down from 60 U remaining).

For medical devices such as a wearable medication delivery pump, where some or all of the components are disposable for ease of use and cost effectiveness, adding another component for measuring the user fill volume and related increased cost and complexity to the medical delivery device is undesirable. A need therefore exists for accurate detection of the user fill volume in the reservoir of the medication delivery device having an infusion pump system without adding new components and thereby increasing infusion pump complexity and cost.

SUMMARY

Exemplary embodiments of the disclosure may address at least the above problems and/or disadvantages, as well as other not described above. Also, exemplary embodiments are not required to overcome the disadvantages described above, and may not overcome any of the problems described above.

The matter exemplified in this description are provided to assist in a comprehensive understanding of exemplary embodiments of the disclosure. Accordingly, those of ordinary skill in the art will recognize that various changes and modifications of the embodiments described herein can be made without departing from the scope and spirit of the disclosure. Also, descriptions of well-known functions and constructions are omitted for clarity and conciseness.

In accordance with an example aspect of the present disclosure, a medication delivery device includes an infusion pump system having a reservoir, an insertion mechanism, a fluid path between the reservoir and the insertion mechanism, a plunger inside the reservoir, and a pump drive mechanism coupled with the reservoir, and further includes a processing device configured to determine a user fill volume of a fluid medication by analyzing a location of the plunger with respect to the reservoir when a fill of the fluid medication is completed.

In accordance with a further example aspect of the present disclosure, the processing device is configured to determine the location of the plunger by sensing a pressure inside the reservoir. The infusion pump system further includes a pressure sensor sensing the pressure inside the reservoir.

In accordance with a further example aspect of the present disclosure, the fluid path is selectively blocked when the fill of the fluid medication is completed.

In accordance with a further example aspect of the present disclosure, the processing device measures an initial position of the pump drive mechanism.

In accordance with a further example aspect of the present disclosure, the processing device activates the pump drive mechanism moving the plunger with respect to the reservoir and the processing device measures a movement of the pump drive mechanism from the initial position to when the fill of the fluid medication is completed.

In accordance with a further aspect of the present disclosure, a current position of the pump drive mechanism is determined when a pressure inside the reservoir is greater than a threshold pressure.

In accordance with a further example aspect of the present disclosure, the processing device is configured to determine the user fill volume by calculating a difference between the initial position and the current position of the pump drive mechanism.

In accordance with further example aspects of the present disclosure, the processing device is configured to determine the location of the plunger by sensing an electric current in the pump drive mechanism, a force applied to the pump drive mechanism, and a torque applied to a motor of the pump drive mechanism.

In accordance with further example aspect of the present disclosure, the processing device is configured to determine the location of the plunger by sensing a flow of the fluid medication in the fluid path. Further, the medication delivery device can include a flow sensor sensing the flow of the fluid medication in the fluid path.

In accordance with a further example aspect of the present disclosure, the infusion pump system further includes a pusher connected to the pump drive mechanism and selectively coupled with the plunger inside the reservoir. Further, in an example implementation, the plunger can be decoupled from the pump drive mechanism while the fluid medication is filled in the reservoir such that the plunger can move, or be moved, freely.

BRIEF DESCRIPTION OF THE DRAWINGS

The above and/or other example aspects and advantages of the present disclosure will become apparent and more readily appreciated from the following description of example embodiments, taken in conjunction with the accompanying drawings in which:

FIG. 2B is a perspective top view of the fluid medication delivery device of FIG. 1, with the cover removed and constructed in accordance with an exemplary embodiment of the present disclosure;

FIG. 4 is a block diagram of example components of a fluid medication delivery device constructed in accordance with an exemplary embodiment of the present disclosure;

FIG. 8 is a diagrammatic representation of a user fill volume detection system and methodology according to exemplary embodiment of the present disclosure.

Throughout the drawing figures, like reference numbers will be understood to refer to like elements, features, and structures.

DETAILED DESCRIPTION OF EXEMPLARY EMBODIMENTS

Figure 1:
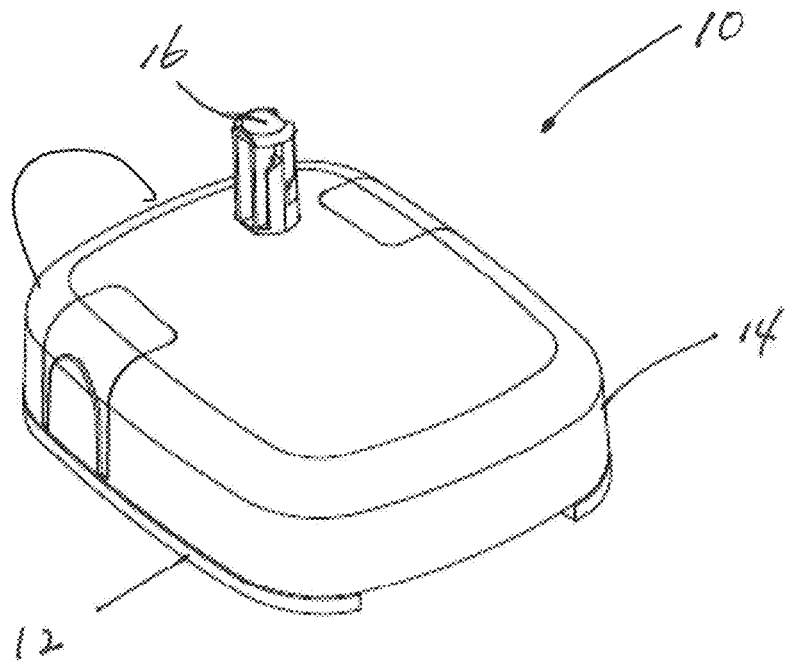
FIG. 1 is a perspective view of a wearable fluid medication delivery device constructed in accordance with an exemplary embodiment of the present disclosure.

Referring now to the drawings, wherein like reference numerals designate identical or corresponding parts throughout the several views, embodiments of the present disclosure are described as follows.

It will be understood that the terms "include," "including," "comprise," and/or "comprising," when used in this specification, specify the presence of stated features, integers, steps, operations, elements, and/or components, but do not preclude the presence or addition of one more other features, integers, steps, operations, elements, components, and/or groups thereof.

It will be further understood that, although the terms, "first," "second," "third," etc., may be used herein to describe various elements, components, regions, layers and/or sections, these elements, components, regions, layers and/or sections may not be limited by these terms. These terms are only used to distinguish over element, component, region, layer or section from another element, component, region, layer or section.

As used herein, the term "and/or" includes any and all combinations of one or more of the associated listed items. Expressions such as "at least one of," when preceding a list of elements, modify the entire list of elements and do not modify the individual elements of the list. In addition, the terms such as "unit,"-er (-or)," and "module" described in the specification refer to an element for performing at least one function or operation, and may be implemented in hardware, software, or the combination of hardware and software.

Various terms are used to refer to particular system components. Different companies may refer to a component by different names—this document does not intend to distinguish between components that differ in name but not function.

Matter of these exemplary embodiments that are obvious to those of ordinary skill in the technical field to which these exemplary embodiments pertain may not be described here in detail. In addition, various features of the exemplary embodiments can be implemented individually or in any combination or combinations, and would be understood by one of ordinary skill in the art of medicament delivery devices.

The example embodiments of a user fill volume detection algorithm described below are useful for utilizing one of the occlusion detection systems having an infusion pump system. The infusion pump system is generally understood to be a type of pump that works on the principle of filling a chamber (for example, with liquid medication from a reservoir) in one stage and then emptying the fluid from the chamber (for example, to a delivery device such as a cannula deployed in a patient) in another stage. In the exemplary embodiment of the present disclosure, further, the user fill volume detection system described below employs a number of technical principles such as: (a) a fluid detection methodology for measuring a pressure inside the chamber of the reservoir; (b) a plunger decoupled from a pump drive mechanism; (c) a pump drive mechanism that starts in a known state (known position); and (d) a fluid path which can be selectively blocked during initialization (for example, with a downstream vent).

For illustrative purposes, as shown in an exemplary embodiment of FIGS. 1, 2A, 2B, and 3A-3C, reference is made to an example implementation of a medication delivery device 10 having a reciprocating plunger-pump type. FIG. 1 is a perspective view of the wearable medication delivery device 10 including a baseplate 12, a cover 14, and an insertion mechanism 16. The insertion mechanism 16 is configured to insert a cannula into a skin of the patient to deliver a fluid medication.

Figure 2A:
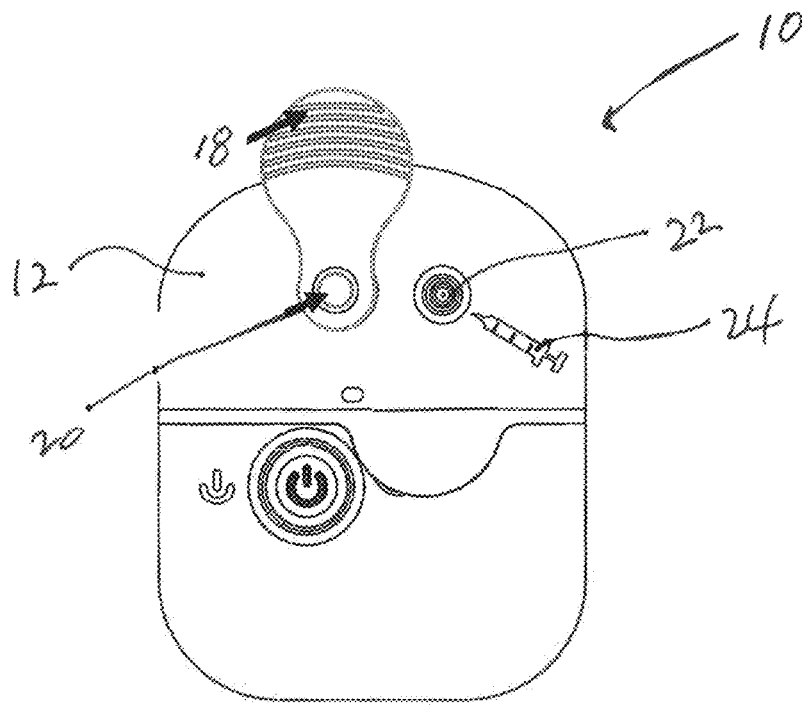
FIG. 2A is a plan bottom view of the fluid medication delivery device of FIG. 1, constructed in accordance with an exemplary embodiment of the present disclosure.

FIG. 2A is a plan view of the outer surface of the base plate 12 in the medication delivery device 10. In an exemplary implementation illustrated in FIG. 2A, the medication delivery device 10 further includes a fill tab 18 with a downstream venting membrane 20 to provide pressure equalization and also a sterile environment, and a fill port 22 to receive a needle of a filled syringe 24. As illustrated in FIG. 2B, medication delivery device 10 includes a reservoir 26 connected to the fill port 22 via an inlet fluid path such that the reservoir 26 can be filled with a fluid medication by a user inserting the needle of the filled syringe 24 into the fill port 22. It is to be understood that the medication delivery device 10 can be filled with a fluid medication using different mechanisms and methods.

FIG. 2B is a perspective view of the medication delivery device 10 of FIG. 1 with the cover 14 removed. The base plate 12 supports the insertion mechanism 16, a motor 28, a power source such as a battery 30, a printed circuit board (PCB) 32 having a microcontroller 31, a memory 33, and other electronic components, and reservoir 26 for storing the fluid medication to be delivered to the patient (or user) via an outlet fluid path 34 from an outlet port of the reservoir 26 through the insertion mechanism 16. In an exemplary implementation reservoir 26 has an inlet port connected to the fill port 22 via the inlet fluid path to receive the fluid medication. As shown in FIG. 2B, the reservoir 26 contains a plunger 36 having a stopper assembly. The proximal end 25 of the reservoir 26 is also provided with a plunger driver assembly 38 having, according to an exemplary implementation, a gear anchor 40, a telescoping screw system (not shown), and a nut 41 that is rotated via a gear train 42 operately connected to the motor 28. In an exemplary implementation of FIG. 2B, the gear anchor 40 arranged in the proximal end 25 of the reservoir 26 is rotationally connected to the nut 41, which is engaged with the gear train 42 operated by the motor 28. Further, the gear anchor 40 is securely mounted to the base plate 12 to react to forces from the plunger movement and fluid pressure.

Referring to example of FIG. 2B, the medication delivery device 10 can further include a pusher 44 arranged inside the reservoir 26 and positioned between the plunger 36 and the gear anchor 40. In an exemplary implementation, the pusher 44 can be fixedly connected with, for example, a telescoping screw system of the plunger driver assembly 38 such that the pusher 44 is axially moved to push the plunger 36 when the fluid medication inside the reservoir 26 is discharged. As illustrated in FIG. 2B, which shown an example of device 10 in a starting position (before fill), the gear anchor 40 has a front surface that can abut the pusher 44 when the plunger driver assembly 38 is fully retracted, but the gear anchor 40 is not required to abut the pusher 44 depending on the dimensions of the reservoir 26 and the plunger driver assembly 38. In an example implementation, the gear anchor 40 can include at least one aperture or through hole (not shown) for venting, and the pusher 44 can have an opening (s) and/or clearance to allow venting as it moves axially in the reservoir 26.

Figure 3A:
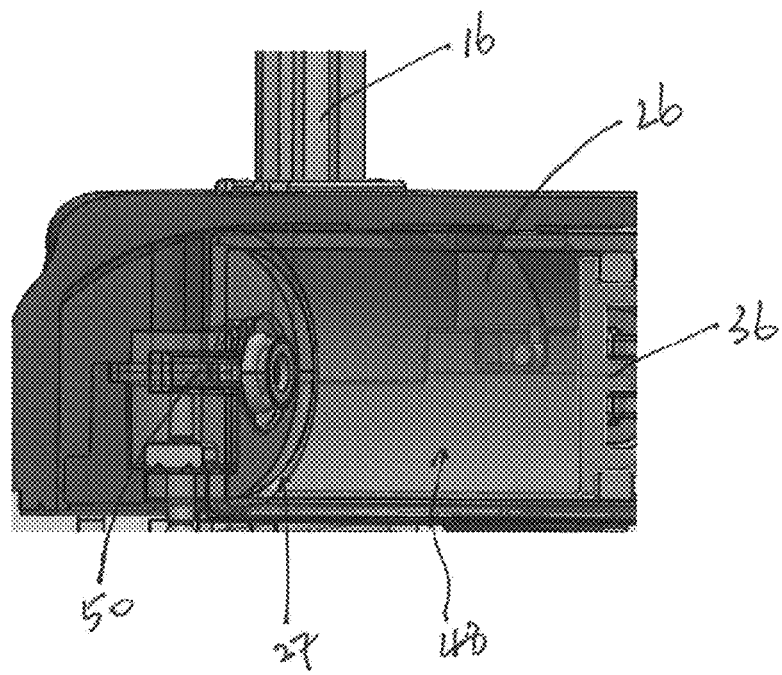
FIG. 3A is a partial side view showing a pressure sensor arranged in the fluid medication delivery device of FIG. 1, according to an exemplary implementation.
Figure 3B:
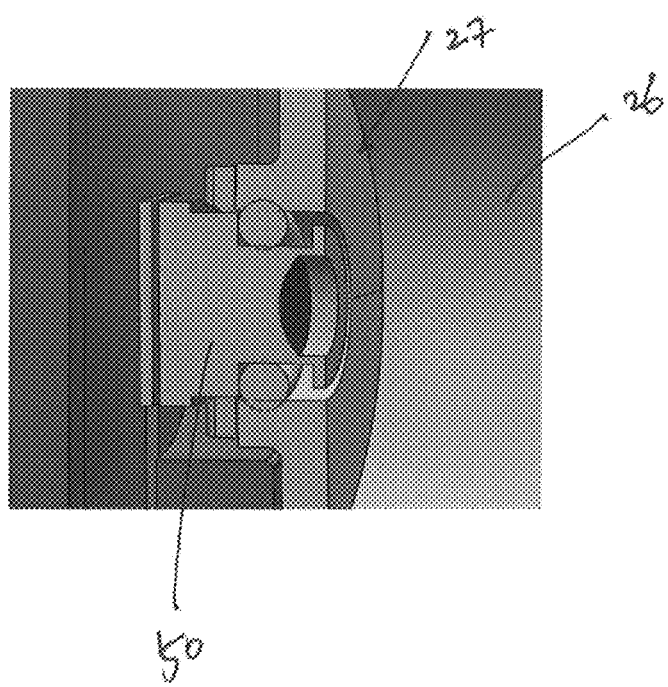
FIG. 3B is a detailed view of the pressure sensor arranged in the fluid medication delivery device of FIG. 3A.
Figure 3C:
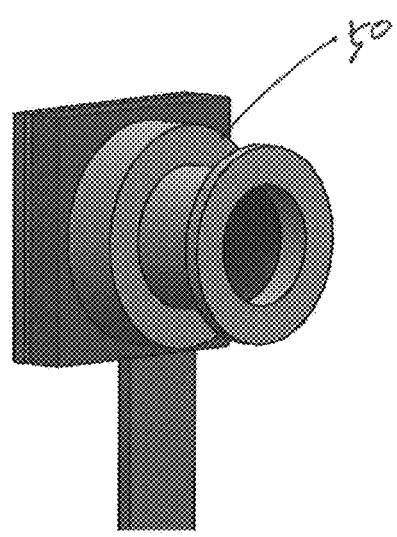
FIG. 3C shows detail on an example of the pressure sensor of FIG. 3A.

FIG. 3A shows an exemplary implementation of a pressure sensor 50, as a component for detection of fluid medication, arranged in the reservoir 26 in accordance with an exemplary embodiment of the present disclosure. FIG. 3B shows the pressure sensor 50 mounted with respect to the distal end 27 (for example in a wall) of the reservoir 26. FIG. 3C shows the pressure sensor 50 configured to measure a pressure inside the chamber portion 48 defined in the reservoir 26 during the operation of the medication delivery device 10. In another exemplary implementation, the pressure sensor 50 can be arranged in other areas where the pressure of the chamber portion 48 can be measured. Further, the pressure sensor 50 can be configured to communicate with the microcontroller 31 of the PCB 32 via a wired interface or wirelessly such that the pressure measured by the sensor 50 can be used to determine the user fill volume of the fluid medication in the reservoir 26.

FIG. 4 is a system diagram 100 that illustrates an example implementation of components in an example medication delivery device 10 having an infusion pump system of FIGS. 1, 2A, 2B, and 3A-3C for detecting a user fill volume of the fluid medication. Referring to example of FIG. 4, medication delivery device 10 can include a power storage sub-system 102, a fluidics sub-system 104, and an electronics sub-system 106 for controlling operations of components in the fluidics sub-system 104 such as the insertion mechanism 16 for deploying the cannula for inserting into an infusion site on a patient's skin. The power storage sub-system 102 includes a power source, such as one or more batteries 30, for example, for providing power to components in the electronics and fluidics sub-systems 104 and 106. The fluidics sub-system 104 includes a motor 28, a gear train 42, a pump drive mechanism 37 including a plunger drive assembly 38 for controlling the pusher 44 including selectively the plunger 36, and the outlet fluid path 34. Further, for example, the fluidic sub-system 104 includes the fill port 22 for filling the reservoir 26 with a fluid medication.

Further, the electronics sub-system 106 includes the microcontroller 31 with an integrated or separate memory device 33 for controlling the infusion pump system to detect the user fill volume of the fluid medication filled in the reservoir 26. A user fill volume detection algorithm (see FIG. 6) in accordance with illustrative embodiments can be provided to the microcontroller 31 to measure locations of the plunger driven by the pump drive mechanism 37 and determine the amount of the fluid medication inside the reservoir 26, which is filled by the patient (or user).

Figure 5A:
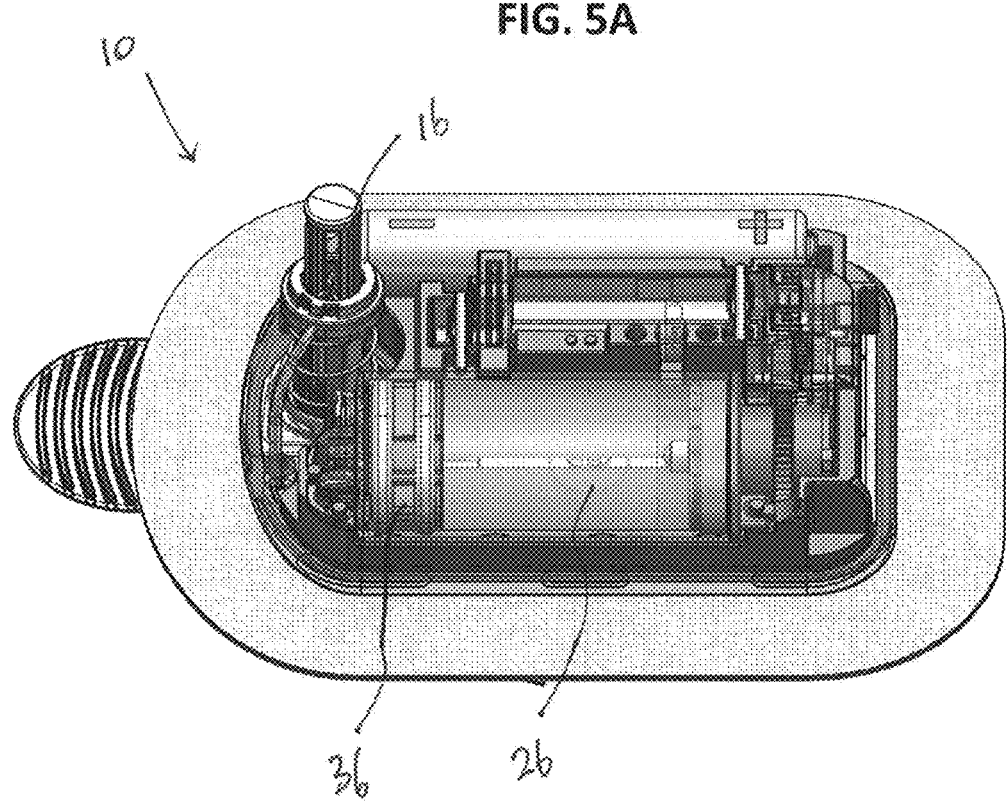
FIGS. 5A, 5B, and 5C are perspective top views of a fluid medication delivery device with cover removed and constructed in accordance with an exemplary embodiment and shown in different stages of filling a reservoir.
Figure 5B:
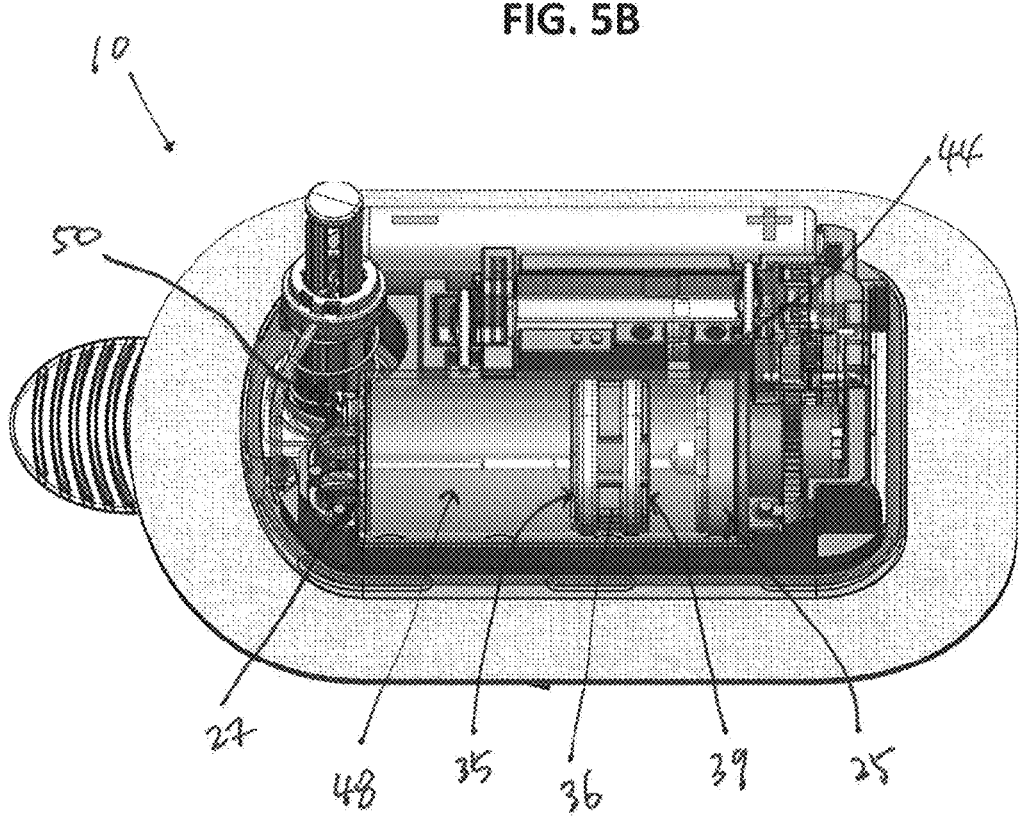
Figure 5C:
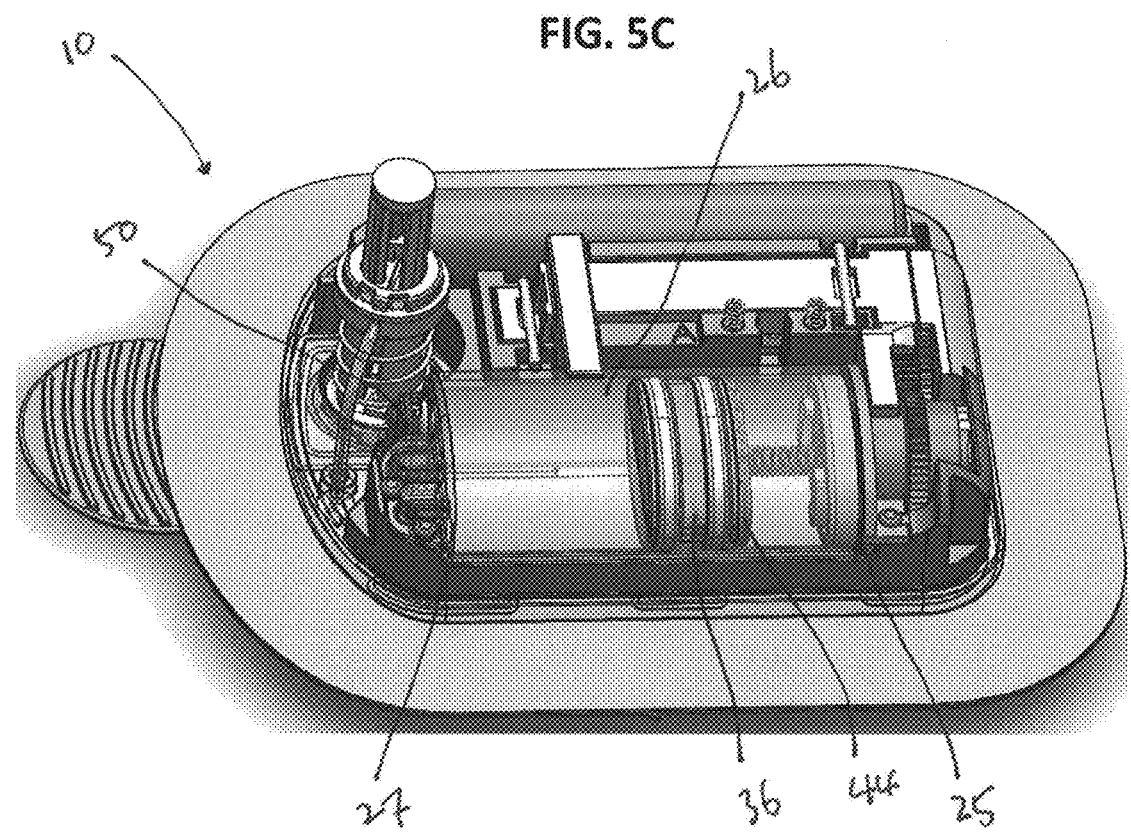

FIGS. 5A, 5B, and 5C illustrate an exemplary method for determining the user fill volume of the fluid medication filled in the reservoir 26 of the exemplary medication delivery device 10 described in FIGS. 1 through 3A. FIG. 5A shows an initial state of the reservoir before filling the fluid medication in the medication delivery device 10 such that the reservoir 26 is empty of any fluid medication and the plunger 36 is positioned at its most distal position inside the reservoir 26. A user (or patient) can insert the needle of a filled syringe 24 into the fill port 22 provided in the baseplate 12 (see FIG. 2) that has the inlet fluid path from the fill port 22 to the reservoir 26. As the fluid medication is transferred from the syringe 24 to the reservoir 26 via the inlet fluid path, the volume of the fluid chamber portion 48 defined in the reservoir 26 by the front (fluid facing) side 35 of the plunger 36 increases (see FIG. 5B). The plunger 36 has the stopper assembly formed of an elastic material to prevent leakage of any fluid medication retained in the fluid chamber portion 48 of the reservoir 26 such that the plunger 36 is configured to seal the fluid medication from entering the portion of the reservoir 26 defined by a rear side 39 of the plunger 26.

Figure 5D:
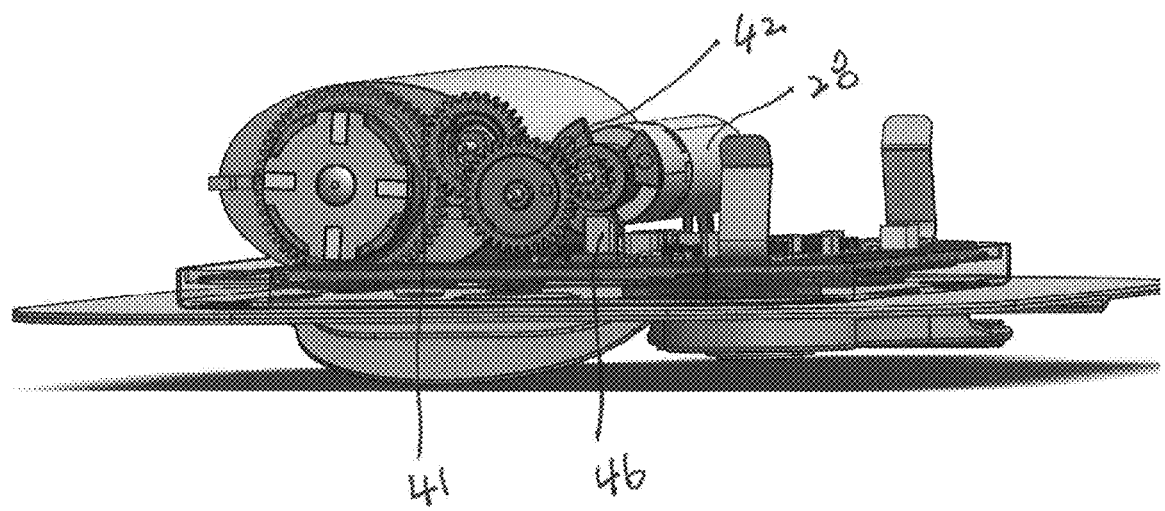
FIG. 5D is a side-perspective view of the fluid medication delivery device of FIG. 5A.

As shown in FIG. 5B, after the fill of the fluid medication is completed, the microcontroller 31 performs an initialization process for determining the volume of the fluid medication, which is filled in the reservoir 26. When the fluid medication is filled in the reservoir 26, the plunger 36 freely moves to a first location between the proximal end 25 and the distal end 27 of the reservoir 26. After filling the fluid medication, the fluid paths is blocked such that any fluid medication is not allowed to flow in the infusion pump system. Referring to example of FIG. 5B, once the fill of the fluid medication has been completed and the fluid paths are sealed, the pump drive mechanism begins driving the pusher 44 inside the reservoir 26 from the known position of the pump drive mechanism, which is defined in an initial position (Xo) of the pump drive mechanism, and the microcontroller 31 keeps track of how much the pusher 44 connected to the pump drive mechanism 37 has advanced from its initial position (Xo) for example by reading a drive encoder 46 arranged inside the cover 14 of the medication delivery device 10 (see FIG. 5D). As shown in FIG. 5D, in an exemplary implementation, the drive encoder 46 can be connected to the gear train unit 42 and provide feedback to the microcontroller 31 by sensing the pump motor action and also the rotation of the drive nut 41.

As shown in FIG. 5C, the pump drive mechanism continues to drive the plunger 36 that contacts, for example couples to, pusher 44 until the pressure is generated in the fluid path including the reservoir as the plunger 36 is urged toward the distal end 27 of the reservoir 26 by pusher 44. As described above, the pressure of the fluid path including the reservoir 26 is sensed by the pressure sensor 50 (see FIG. 3A) in accordance with an exemplary embodiment of the present disclosure. When the pressure detected by the pressure sensor 50 is greater than, for example predetermined, threshold pressure ($P_{thresh}$) according to an exemplary algorithm of FIG. 6, the plunger 36 is stopped at a second location within reservoir 26, and the microcontroller 31 measures the advanced movement of the pump drive mechanism coupled to the plunger 36 at the second location of the plunger 36 as a current position (Xn) of the pump drive mechanism 37. Once the fluid path including the reservoir 26 is pressurized, which means that the detected pressure is greater than the predetermined threshold pressure ($P_{thresh}$) as described above, it has been understood that all drivetrain components in the pump drive mechanism 37 have been fully engaged with the plunger 36 such that the fluid medication inside the reservoir 26 can be pushed for delivery. At this stage, the microcontroller 31 can determine the user fill volume of the reservoir 26 by calculating the difference between the initial position (Xo) and the current position (Xn) of the pump drive mechanism 37. Accordingly, a volume available to be dispensed can be calculated by taking into account the difference between the initial position (Xo) and the current position (Xn), which volume corresponds to the amount of the fluid medication filled by the patient (or user).

Figure 6:
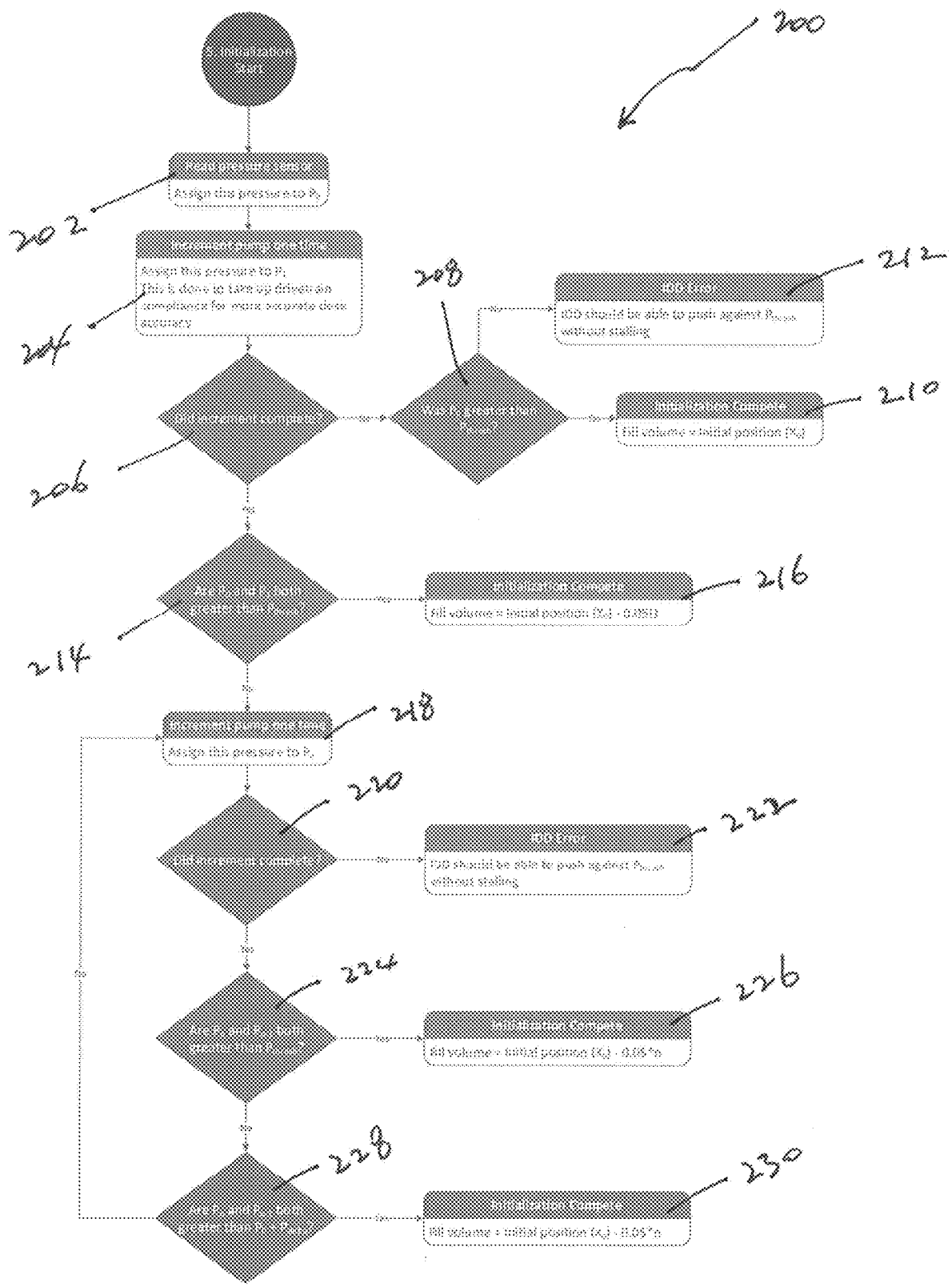
FIG. 6 is a flow chart of illustrative operations of an exemplary fluid medication delivery device performing a user fill volume detection algorithm in accordance with an illustrative embodiment of the present disclosure.

FIG. 6 is a flow chart diagrammatically illustrating an example of operations 200 of a medication delivery device 10 performing a user fill volume detection in accordance with exemplary implementations of embodiments of the present disclosure, which can be implemented using a microcontroller 31, or other processing device for controlling or monitoring pump operation of the medication delivery device 10. When the user (or patient) fills the fluid medication in the device, the downstream fluid path fills up to the vent first and expels all air in the downstream fluid path before the plunger starts moving. The majority of the volume filled by the user (for example, the volume of fluid chamber portion 48 illustrated in FIG. 5B) moves the plunger 36 from a distal end 27, or front, of reservoir 26 to an unknown location between the distal end 27 (for example, corresponding to 0 U fill) and a starting known position (for example, corresponding to 310 U fill). Referring for example to FIG. 5B, an initialization processing of operation 200 starts with the outlet fluid path 34 being blocked to liquid flow (for example by a selectively downstream venting membrane 20), the reservoir plunger 36 being disposed at the unknown location, and pusher 44 connected to the pump drive mechanism 37 starting in a known position (Xo).

Referring to example of FIG. 6, after the user has confirmed that fill is completed, the microcontroller 31 reads the pressure and assigns this pressure to $P_0$ (Bock 202). Then, in an exemplary implementation, the pump drive mechanism 37 starts driving the pusher 44 such that pusher 44 connected to the pump drive mechanism 37 moves toward the distal end 27 of the reservoir 26 one step increment to take up the drivetrain compliance in the medication delivery device 10, the microcontroller 31 reads the pressure and assigns this pressure to $P_1$ (Bock 204), and checks if the one step increment was completed (Block 206). If the one step increment was not completed and if the pressure is generated and sensed, then microcontroller 31 analyzes the pressure ($P_0$) to determine if the sensed pressure ($P_0$) is greater than a predetermined threshold pressure ($P_{thresh}$) (for example, 15 psi) (Block 208). If the pressure ($P_0$) is greater than the threshold pressure ($P_{thresh}$), then the plunger has been fully bottomed out, the initialization process is completed, and the user fill volume is determined (Block 210) to be at the initial position (Xo) of the pump drive mechanism, which is 310 U in the example of FIG. 6. If the pressure ($P_0$) is not greater than the predetermined threshold pressure ($P_{thresh}$) (Block 208), there may be a potential error in delivery device operation because the pump drive mechanism 37 should be able to advance the pusher 44 until measured pressure is greater than $P_{thresh}$ without stalling (Block 212).

Referring further to example of FIG. 6, if the one step increment has been complete (Block 206), the microcontroller 31 analyzes both pressures ($P_0$ and $P_1$) to determine if the pressures ($P_0$ and $P_1$) are each greater than the predetermined threshold pressure ($P_{thresh}$), (Block 214). If both pressures ($P_0$ and $P_1$) are each greater than the threshold pressure ($P_{thresh}$), the initialization process is complete and the user fill volume is determined by subtracting a current position (X1) of the pump drive mechanism 37 with one step increment from the initial position (Xo) (Block 216). In the exemplary embodiment of the present disclosure, the user fill volume is determined by subtracting 0.05 U from 310 U when one step increment of the pump drive mechanism 37 is completed. If the pressures ($P_0$ and $P_1$) are not greater than the threshold pressure ($P_{thresh}$), the microcontroller 31 continues to advance the pusher 44 connected to the pump drive mechanism 37 with a step increment (Block 218).

As described above, the microcontroller 31 is programmed to continue to determine the user fill volume of the medication delivery device according to the algorithm of FIG. 6. The pump drive mechanism advance the pusher by one step increment (Block 218) and the microcontroller 31 checks if the one step increment is completed (Block 220). When the one step increment of the pump drive mechanism is completed, the microcontroller 31 checks if both pressures ($P_n$ and $P_{n-1}$) measured at the current position with one step increment (n-step increment) and the previous position before incrementing one step (n−1 step increment) are greater than the predetermined threshold pressure ($P_{thresh}$) (Block 224). In Block 220, if the one step increment is not completed, the microcontroller 31 checks if the pump drive mechanism is able to push against the threshold pressure without stalling (Block 222). In Block 224, if both pressures ($P_n$ and $P_{n-1}$) are each greater than the threshold pressure ($P_{thresh}$), the microcontroller 31 determines that the initialization process is completed and the user fill volume is calculated by subtracting the current position (Xn) from the initial position (Xo) of the pump drive mechanism. For example, in the exemplary embodiment of the present disclosure, the user fill volume is calculated by subtracting 0.05*n from the initial position (for example, 310 U) (Block 226). In particular, in an exemplary implementation, as described with reference to FIG. 6, on step increment of a pusher 44 correspond to 0.05 U volume displacement.

Further, in Block 224, if both pressures ($P_n$ and $P_{n-1}$) are not greater than the threshold pressure ($P_{thresh}$), the microcontroller 31 also checks if both pressures ($P_n$ and $P_{n-1}$) are greater than ($P_0$ and $P_{delta}$) (for example, $P_{delta}$=3 psi) (Block 228). If both pressures ($P_n$ and $P_{n-1}$) are greater than the pressures ($P_0$ and $P_{delta}$), the microcontroller 31 determines that the initialization process is completed and the user fill volume is calculated by subtracting the current position (Xn) from the initial position (Xo) of the pump drive mechanism. For example, in the exemplary embodiment of the present disclosure, the user fill volume is calculated by subtracting 0.05*n from the initial position (for example, 310 U) (Block 230). As shown in FIG. 6, if the predetermined threshold pressure has not been reached, the microcontroller 31 begins incrementing according to the procedure 200. It continues to increment until a pressure builds up. When the pressure criteria have been met, the microcontroller 31 stops the increments and determines the number of remaining increments corresponding to the user's fill volume by subtracting the current position from the initial position of the pump drive mechanism.

Figure 7:
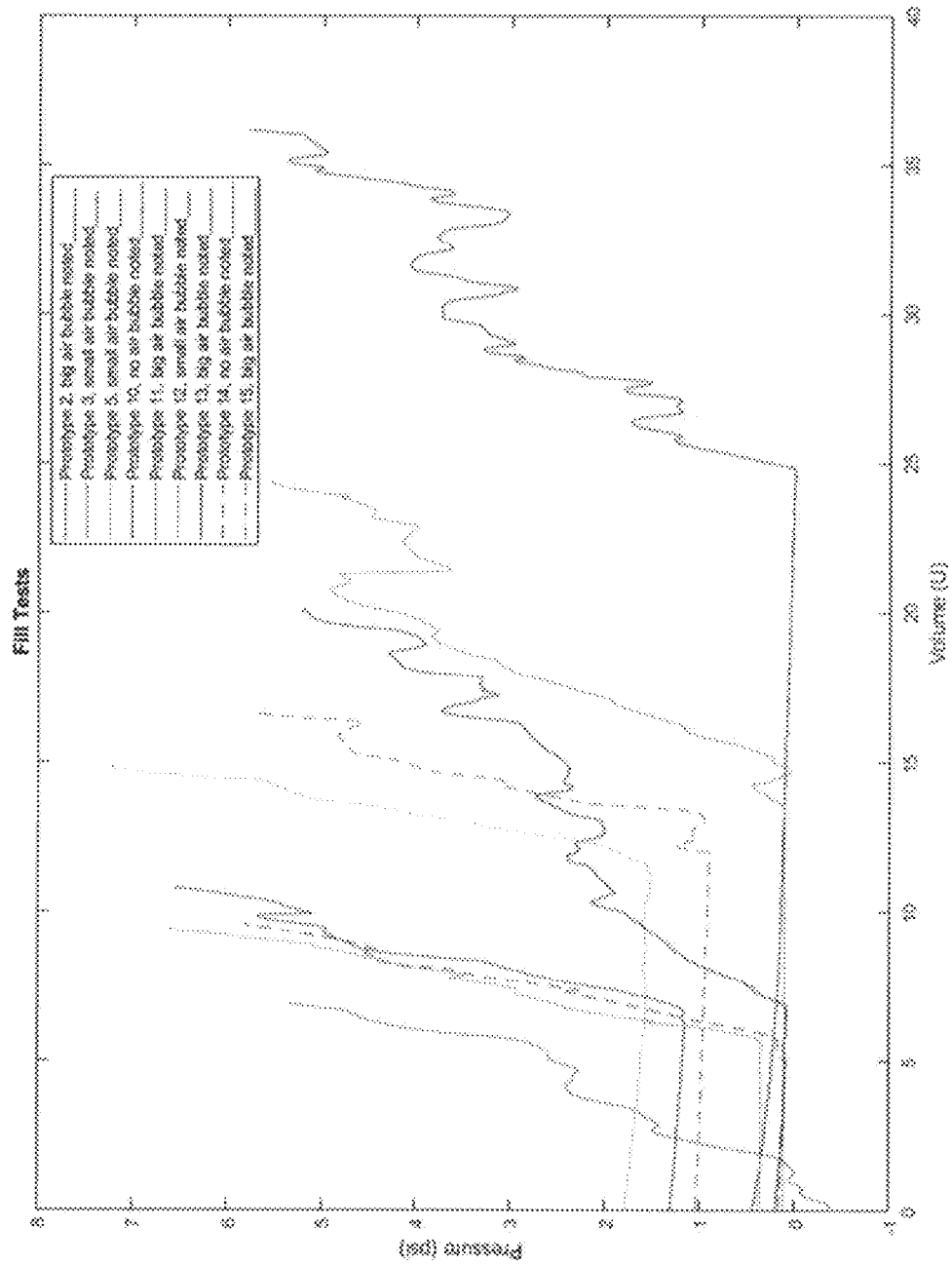
FIG. 7 depicts an example of pressure data measurements inside the reservoir from fluid medication delivery devices according exemplary embodiments of the disclosure.

FIG. 7 depicts pressure data measurements in the reservoir of various medication delivery devices, non-limiting examples of such devices are described above with reference to FIGS. 1-5C, performing the initialization process according to the procedure of FIG. 6. When the drivetrain of the medication delivery device is incrementing, the medication delivery device takes a pressure reading after every increment. As shown in the example of FIG. 7, the pressure data measurements have very little noise before the pusher connected to the pump drive mechanism is selectively coupled with the plunger, and also very clear inflection points when the pusher is fully engaged with the plunger. After that, the pressure data measurements show that the pressure inside the reservoir builds immediately and is detectable, and also the pressure continues to build without leaking or flow through the downstream venting membrane. Accordingly, as described above, the user fill volume detection system in the medication delivery devices can determine the user fill volume by measuring the increments of the pump drive mechanism with the pressure sensed inside the reservoir.

It is to be understood that the example embodiments described herein can be subject to operative variations and alternative configurations to measure the user fill volume. The user fill volume detection system could use any pressure sensing method or surrogate like current sensing, force sensing, membraned sensing, or torque sensing. For example, because current should correspond to pressure/force/torque, etc. instead of setting a pressure limit, the algorithm of FIG. 6 could be applied to current signals instead of pressure signals. Another variation could involve using a flow sensor instead of a pressure sensor. If utilizing the flow sensor, the device would be required to have a known downstream compliance or a selectively leaking vent. The flow sensor would read no flow until the pump drive mechanism engages the plunger at which point, there would be flow through the sensor which is expanding the downstream fluid path or there would be flow through the downstream vent indicating that the system has been fully engaged and primed.

According to an example implementation, another variation which can be configured by setting up a system similar to those described above with reference to, for example, FIGS. 5A-5C, where, instead of measuring pressure, the pump drive mechanism would increment during filling until the entire drive mechanism stalls. As long as the stall condition can only happen when the drivetrain is bottomed out and the system is pressurized, the fill volume can be calculated.

Another example embodiment of a user fill volume detection system of the present disclosure provides implementing configurations such as those decided above with reference to FIGS. 1-7, where medication is dispensed from a chamber using a syringe-like plunger action, can be described with reference to FIG. 8. In an exemplary implementation, prior to filling the device, a plunger 36 is disconnected from a pusher 44 and is located at the front (distal end) 27 of reservoir 26 (the empty position). As fluid is injected into device 10, the plunger 36 is pushed back as the reservoir 26 fills and eventually is stopped when it reaches the pusher 44. The volume of fluid in that the reservoir can accept can be adjusted by pre-positioning the pusher 444 at the desired max volume.

Referring to FIG. 8, an example implementation is described with reference to a chart 300 that illustrates how the user can measure the fill volume and communicate with the medication delivery device 10 according to exemplary embodiments of the present disclosure. In step 301, the user has the medication delivery device 10, and in step 302, the user having a controller installed in a personal device 60 (for example, an application installed on a smart phone (see FIG. 4)) for wirelessly communicating with the medication delivery device 10 pairs the controller with an electronic subsystem 106 of the medication delivery device 10.

In step 303, further, according to an instruction of the controller installed in the personal device 60, the user inputs the quantity of intended fill volume. In step 304, the controller receiving the information of the fill volume records the volume and instructs the medication delivery device 10 to move a pusher 44 to the location that limits the fill volume to the desired quantity. Prior to filling the delivery device 10, the plunger 36 is disconnected from the pusher rod and is located at the distal end 27 of the reservoir 26 which is the empty position of the plunger 36 as shown in FIG. 5A. Finally, in step 305, the user (or patient) can now fill the medication delivery device 10 with the syringe 24 or the filling device such that the detection of the fill volume in the medication delivery device is achieved. As liquid medication is injected into the medication delivery device 10, the plunger 36 is pushed back as the reservoir fills and eventually is stopped when it reaches the pusher rod. Further, in the steps 303 and 304, the volume that the reservoir can accept can be adjusted by pre-positioning the pusher rod at the desired max volume.

According to yet further exemplary embodiments of the disclosure, plunger 36 contact with pusher 44 can be detected instead of, or in conjunction with, building pressure or generating flow. In exemplary implementations, any pressure sensing method or surrogate like current sensing, force sensing, membrane deflection, or torque sensing can be used. For example, because current can correspond to pressure/force/torque/etc., instead of setting a pressure limit, the processing and hardware described with reference to FIG. 6, could be applied to current signals instead of pressure signals.

For example, if measuring force/torque/current, the medication delivery device (for example, Insulin Delivery Device) should see an increase in the signal when the pusher contacts the plunger because now the pump drive mechanism must push against the plunger friction force in addition to the torques/forces being driven up the that point. This detection system can have an the advantage of not needing to build any pressure. Further, another potential advantage of such a design is that it does not rely on a selectively blocked downstream path. For example, if the medication delivery device is filled through the dispense needle, such method of fill detection would still work.

As described above, exemplary embodiments of the present disclosure provide system components and methods for detecting a user fill volume of a fluid medication in a pump infusion system. Such user fill volume detection results can be implemented using existing infusion pump system present in most medication delivery devices. Further, the user fill volume detection can be implemented without an additional component. For example, a microcontroller or other processing device for controlling pump operation can be further controlled to determine the user fill volume by sensing pressure of the reservoir existed in the device.

Having an integrated method that detects fill volume using existing hardware provides a technical solution to the above technical problems such that users do not have to keep track of and carry a separate filling device to perform the equivalent system functions. For example, embodiments of the present disclosure can be applied to and can also have an advantage over some known devices using a switch which is triggered during fill at a specific fill amount (for example, 60 U). By monitoring the switch during dispense, it detects when the switch is disengaged. From the disengagement point, such devices count down to zero/empty. Because of this design, a drawback of such devices is inability to calculate the fill volume and to confirm the fill volume with the user. It also cannot display the remaining volume to the user until the remaining volume is equal to or less than the volume corresponding to the switching point. The accuracy of such devices' fill/empty detection is dependent on the accuracy of the switching. In the examples of described herein, the accuracy of the fill volume detection can be determined by the dose encoding components configured to be accurate in order to ensure infusion dose accuracy. Further, other exemplary devices can be configured without a fill volume feedback and rely on the user to accurately input the fill volume information. Configurations for measure fill volume as described in above exemplary implementations can be advantageous for such devices.

The components of the illustrative devices, systems and methods employed in accordance with the illustrated embodiments can be implemented, at least in part, in digital electronic circuitry, analog electronic circuitry, or in computer hardware, firmware, software, or in combinations of them. These components can be implemented, for example, as a computer program product such as a computer program, program code or computer instructions tangibly embodied in an information carrier, or in a machine-readable storage device, for execution by, or to control the operation of, data processing apparatus such as a programmable processor, a computer, or multiple computers.

A computer program can be written in any form of programming language, including compiled or interpreted languages, and it can be deployed in any form, including as a stand-alone program or as a module, component, subroutine, or other unit suitable for use in a computing environment. A computer program can be deployed to be executed on one computer or on multiple computers at one site or distributed across multiple sites and interconnected by a communication network. Also, functional programs, codes, and code segments for accomplishing the illustrative embodiments can be easily construed as within the scope of claims exemplified by the illustrative embodiments by programmers skilled in the art to which the illustrative embodiments pertain. Method steps associated with the illustrative embodiments can be performed by one or more programmable processors executing a computer program, code or instructions to perform functions (for example, by operating on input data and/or generating an output). Method steps can also be performed by, and apparatus of the illustrative embodiments can be implemented as, special purpose logic circuitry, for example, an FPGA (field programmable gate array) or an ASIC (application-specific integrated circuit), for example.

The various illustrative logical blocks, modules, and circuits described in connection with the embodiments disclosed herein may be implemented or performed with a general purpose processor, a digital signal processor (DSP), an ASIC, a FPGA or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, for example, a combination of a DSP and a microprocessor, a plurality of microprocessors, one or more microprocessors in conjunction with a DSP core, or any other such configuration.

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for executing instructions and one or more memory devices for storing instructions and data. Generally, a computer will also include, or be operatively coupled to receive data from or transfer data to, or both, one or more mass storage devices for storing data, for example, magnetic, magneto-optical disks, or optical disks. Information carriers suitable for embodying computer program instructions and data include all forms of non-volatile memory, including by way of example, semiconductor memory devices, for example, electrically programmable read-only memory or ROM (EPROM), electrically erasable programmable ROM (EEPROM), flash memory devices, and data storage disks (for example, magnetic disks, internal hard disks, or removable disks, magneto-optical disks, and CD-ROM and DVD-ROM disks). The processor and the memory can be supplemented by, or incorporated in special purpose logic circuitry.

Those of skill in the art would understand that information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

Those of skill would further appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of claims exemplified by the illustrative embodiments. A software module may reside in random access memory (RAM), flash memory, ROM, EPROM, EEPROM, registers, hard disk, a removable disk, a CD-ROM, or any other form of storage medium known in the art. An exemplary storage medium is coupled to the processor such the processor can read information from, and write information to, the storage medium. In the alternative, the storage medium may be integral to the processor. In other words, the processor and the storage medium may reside in an integrated circuit or be implemented as discrete components.

Computer-readable non-transitory media includes all types of computer readable media, including magnetic storage media, optical storage media, flash media and solid state storage media. It should be understood that software can be installed in and sold with a central processing unit (CPU) device. Alternatively, the software can be obtained and loaded into the CPU device, including obtaining the software through physical medium or distribution system, including, for example, from a server owned by the software creator or from a server not owned but used by the software creator. The software can be stored on a server for distribution over the Internet, for example.

The above-presented description and figures are intended by way of example only and are not intended to limit the illustrative embodiments in any way except as set forth in the following claims. It is particularly noted that persons skilled in the art can readily combine the various technical aspects of the various elements of the various illustrative embodiments that have been described above in numerous other ways, all of which are considered to be within the scope of the claims.

What is claimed is:

1. A medication delivery device comprising:
   an infusion pump system comprising
   a reservoir comprising a fluid chamber portion,
   an outlet fluid path between the fluid chamber portion of the reservoir and an insertion mechanism,
   an inlet fluid path between the fluid chamber portion of the reservoir and a fill port,
   a plunger inside the reservoir comprising a front side in contact with a fluid medication in the fluid chamber portion, and configured to seal the fluid medication in the fluid chamber portion from entering a portion of the reservoir defined by a rear side of the plunger, and
   a pump drive mechanism coupled with the reservoir;
   a pressure sensor sensing a pressure inside the reservoir; and
   a processing device configured to determine a user fill volume of the fluid medication by analyzing a location of the plunger with respect to the reservoir, wherein
   an initial position of the pump drive mechanism corresponds to the location of the plunger with respect to the reservoir after a fill of the reservoir with the fluid medication is completed when the plunger is stopped with respect to the reservoir and the outlet fluid path and the inlet fluid path are blocked such that any fluid medication is not allowed to flow in the infusion pump system,
   a current position of the pump drive mechanism system corresponds to the location of the plunger with respect to the reservoir when after an initialization of the pump drive mechanism, the outlet fluid path and the inlet fluid path remain blocked, the plunger is advanced with respect to the reservoir, and the pressure inside the reservoir sensed by the pressure sensor is greater than a predetermined threshold value, and
   the processing device determines the user fill volume of the fluid medication with reference to the initial position of the pump drive mechanism and the current position of the pump drive mechanism.

2. The medication delivery device of claim 1, wherein the processing device is configured to determine the location of the plunger by sensing a pressure inside the reservoir.

3. The medication delivery device of claim 1, wherein the processing device measures the initial position of the pump drive mechanism.

4. The medication delivery device of claim 3, wherein the processing device activates the pump drive mechanism moving the plunger with respect to the reservoir, and the processing device measures a movement of the pump drive mechanism from the initial position to when the fill of the fluid medication is completed.

5. The medication delivery device of claim 1, wherein the processing device is configured to determine the user fill volume by calculating a difference between the initial position and the current position of the pump drive mechanism.

6. The medication delivery device of claim 1, wherein the infusion pump system further includes a pusher connected to the pump drive mechanism and selectively coupled with the plunger inside the reservoir.

7. The medication delivery device of claim 1, wherein the plunger is decoupled from the pump drive mechanism while the fluid medication is filled in the reservoir such that the plunger is freely moved inside the reservoir.

8. The medication delivery device of claim 1, wherein the processing device is configured to determine the location of the plunger by sensing an electric current in the pump drive mechanism.

9. The medication delivery device of claim 1, wherein the processing device is configured to determine the location of the plunger by sensing a force applied to the pump drive mechanism.

10. The medication delivery device of claim 1, wherein the processing device is configured to determine the location of the plunger by sensing a torque applied to a motor of the pump drive mechanism.

11. The medication delivery device of claim 1, wherein the processing device is configured to determine the location of the plunger by sensing a flow of the fluid medication in the fluid path.

12. The medication delivery device of claim 1, further comprising a flow sensor sensing the flow of the fluid medication in the fluid path.

13. The medication delivery device of claim 11, further comprising a flow sensor sensing the flow of the fluid medication in the fluid path.

* * * * *